US00PP18007P2

(12) United States Plant Patent

Jonkers et al.

(10) Patent No.: US PP18,007 P2
(45) Date of Patent: Sep. 11, 2007

(54) *IMPATIENS* PLANT NAMED 'SILTE ROSSA'

(50) Latin Name: *Impatiens walleriana*
Varietal Denomination: Silte Rossa

(75) Inventors: Johanna B. Jonkers, Andijk (NL); Erik Smit, Enkhuizen (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/410,386

(22) Filed: Apr. 25, 2006

(51) Int. Cl.
*A01H 5/00* (2006.01)

(52) U.S. Cl. ..... Plt./317
(58) Field of Classification Search ..... Plt./317
See application file for complete search history.

*Primary Examiner*—Kent Bell
(74) *Attorney, Agent, or Firm*—Jondle & Associates P.C.

(57) ABSTRACT

A new *Impatiens* plant particularly distinguished by medium to large, double, rose-shaped, deep-rose flowers borne well-above the foliage, deep-green foliage, an early flowering response, floriferous throughout the summer, and a medium-sized, round and bushy plant habit, is disclosed.

1 Drawing Sheet

Genus and species: *Impatiens walleriana.*
Variety denomination: 'Silte Rossa'.

BACKGROUND OF THE NEW PLANT

The present invention comprises a new and distinct cultivar of *Impatiens,* botanically known as *Impatiens walleriana,* and hereinafter referred to by the cultivar name 'Silte Rossa'. The new cultivar originated from a hybridization made in April 2003 in Andijk, The Netherlands. The female parent was the proprietary deep-pink-flowered *Impatiens* plant 'IDY-14-9' (unpatented), while the male parent was the proprietary salmon-flowered *Impatiens* plant 'IDY-29-2' (unpatented). The seeds produced by the hybridization were sown in Andijk, The Netherlands in July 2003. A single plant selection was chosen for further evaluation and for asexual propagation in October 2003 in Andijk, The Netherlands.

The new cultivar was created in 2003 in Andijk, The Netherlands and has been asexually reproduced repeatedly by vegetative cuttings and tissue culture in Andijk, The Netherlands and Hillscheid, Germany over a two-year period. 'Silte Rossa' has not been observed under all possible environmental conditions. The present invention has been found to retain its distinctive characteristics through successive asexual propagations.

Plants Breeder's Rights for this cultivar were applied for in Canada on Oct. 17, 2005 and with the European Union on Nov. 18, 2005.

SUMMARY OF THE INVENTION

The following are the most outstanding and distinguishing characteristics of this new cultivar when grown under normal horticultural practices in Andijk, The Netherlands, and Hillscheid, Germany.

1. Medium to large, double, rose-shaped, deep-rose flowers;
2. Deep-green foliage;
3. A medium-sized, round and bushy plant habit;
4. An early flowering response; and
5. Floriferous throughout the summer.

DESCRIPTION OF PHOTOGRAPH

This new *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 10-weeks old, grown in a greenhouse in Hillscheid, Germany in late May 2005.

DESCRIPTION OF THE NEW CULTIVAR

The following detailed descriptions set forth the distinctive characteristics of 'Silte Rossa'. The data which defines these characteristics were collected from asexual reproductions carried out in Hillscheid, Germany. The plant history was taken in mid September on 9- to 10-week old un-pinched plants which had been planted as rooted cuttings in 12-cm pots mid-July 2005 and grown in a greenhouse at a minimum temperature of 21° C. Color readings were taken under natural light in the greenhouse. Color references are primarily to the R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens walleriana* Hook.
*Common name.*—*Impatiens.*

Parentage:
*Female parent.*—'IDY-14-9' a proprietary deep-pink-flowered *Impatiens* plant (unpatented).
*Male parent.*—'IDY-29-2', a proprietary salmon-flowered *Impatiens* plant (unpatented).

Growth:
*Growth and branching habit.*—Medium-sized, round, bushy and well-branched.
*Height.*—18.5 cm.
*Width.*—16.5 cm.
*Propagation.*—Terminal tips for cuttings.

*Time to produce a finished flowering plant.*—About 8 weeks for a 12-cm pot.

*Time to initiate and develop roots.*—18 days or less at 22° C.

Branches:

*Average number.*—8.8.

*Length of main branches.*—14 cm to 19 cm.

*Internode length.*—0.5 cm to 1.5 cm.

*Diameter of branches* (*at midpoint*).—0.7 cm.

*Stem color.*—RHS 145A (light green) near the nodes with RHS 184D (reddish) infused towards the base.

Leaves:

*Arrangement.*—Primarily alternate.

*Size.*—Length: 9.8 cm. Width: 5.3 cm.

*Shape.*—Elliptical, broad.

*Margin.*—Crenate, ciliate.

*Apex.*—Acuminate.

*Base.*—Acute or obtuse.

*Color* (*mature leaves*).—General: Dark green. Upper surface: RHS 137A. Lower surface: RHS 138B.

*Color* (*immature leaves*).—Upper side: Near RHS 137A. Lower side: RHS 138B, weakly variable or marbled.

*Texture.*—Smooth, glabrous.

*Venation color.*—Upper surface: Indistinct, RHS 145C near the leaf base. Lower surface: RHS 145B (pale green).

*Petioles.*—Length: Variable, up to 4.5 cm. Diameter: 0.3 cm to 0.4 cm. Color: Upper surface: RHS 145D. Lower surface: RHS 145C. Texture: Glabrous.

Flower buds:

*Shape.*—Ovoid, broad.

*Size.*—Length: 1.3 cm. Diameter: 1.5 cm.

*Color at tight bud.*—Light-pink, RHS 65A or RHS 62B.

Inflorescence:

*Blooming habit.*—Approximately 7 weeks after planting of rooted cuttings.

*Inflorescence type.*—Inflorescences appear solitary in the leaf axils of the upper nodes of the stems.

*Number of flowers per node.*—2 to 4 in various stages of development.

*Flowering season.*—Continuously, mainly from March to October, depending on light intensity.

*Lastingness of the individual blooms on the plant.*—About 5 to 7 days (at 18° C. in a greenhouse in the spring).

*Fragrance.*—None.

*Peduncle.*—Color: RHS 145A to RHS 145B (light green). Size: Length: 5.5 cm. Diameter: 1.5 cm to 3.0 cm (lower end). Texture: Flexible, glabrous.

Flowers:

*Form and shape of corolla.*—Double-type, rose-like.

*Corolla size.*—Length: 3.8 cm. Width: 3.4 cm. Depth: 1.5 cm.

*Number of petals.*—More than 20.

Petals:

*Shape.*—Ovate or cordate.

*Apex.*—Rounded or emarginate.

*Base.*—Attenuate to wide and obtuse.

*Margin.*—Entire.

*Petal size.*—Length: 1.6 cm to 2.0 cm. Width: 1.4 cm to 1.8 cm.

*Color.*—General: Deep rose. Upper surface: RHS 58B to RHS 58C with occasional RHS 53D (deeper red) middle lines. Lower surface: Mainly RHS 52B.

*Texture.*—Smooth, satiny.

Spur:

*Shape.*—Curved, downward directed.

*Color.*—RHS 145B (light green).

*Size.*—Length: 3.0 cm. Diameter: 0.3 cm at the flower end.

Reproductive organs:

*Stamens.*—Not observed.

*Pistils.*—Style and stigma: 5, very short, RHS 8D (pale-yellow). Ovary: 5-celled. Ovary length: 0.6 cm. Ovary color: RHS 143B.

Fruit and seed set: No seed set observed.

Disease and insect resistance: No particular resistance or susceptibility has been observed.

COMPARISON WITH PARENTAL AND COMMERCIAL CULTIVARS

'Silte Rossa' differs from the female parent 'IDY-14-9' (unpatented) by having deep-rose, double flowers, while 'IDY-14-9' has deep-pink, single flowers.

'Silte Rossa' differs from the male parent 'IDY-29-2' (unpatented), by having deep-rose, double flowers, while 'IDY-29-2' has salmon, single flowers.

'Silte Rossa' differs from the commercial cultivar 'Didi Carmine Two' (U.S. Plant Pat. No. 15,619) in that 'Silte Rossa' has deep-rose flowers, while 'Didi Carmine Two' has red-purple flowers. Additionally, 'Silte Rossa' has a lower and more rounded plant habit that 'Didi Carmine Two'.

I claim:

1. A new and distinct cultivar of *Impatiens* plant as shown and described herein.

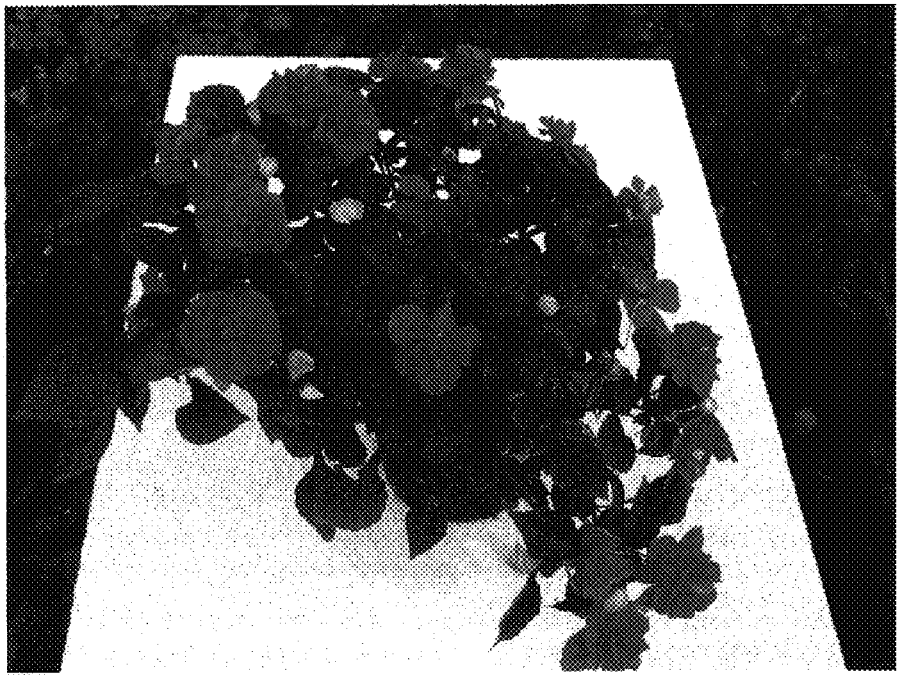

* * * * *